(12) United States Patent
Bacot et al.

(10) Patent No.: US 11,989,942 B2
(45) Date of Patent: May 21, 2024

(54) METHOD FOR CHARACTERIZING A DYNAMIC OCCUPANCY OF A SPACE BY TWO OPPOSING TEAMS OF A GAME AND RELATED SYSTEM

(71) Applicants: Centre National de la Recherche Scientifique, Paris (FR); Ecole Polytechnique, Palaiseau (FR)

(72) Inventors: Vincent Bacot, Issy-les-Moulineaux (FR); Christophe Clanet, Palaiseau (FR)

(73) Assignees: Centre National de la Recherche Scientifique, Paris (FR); Ecole Polytechnique, Palaiseau (FR)

( * ) Notice: Subject to any disclaimer, the term of this patent is extended or adjusted under 35 U.S.C. 154(b) by 530 days.

(21) Appl. No.: 17/432,907

(22) PCT Filed: Feb. 21, 2020

(86) PCT No.: PCT/EP2020/054666
§ 371 (c)(1),
(2) Date: Aug. 20, 2021

(87) PCT Pub. No.: WO2020/169825
PCT Pub. Date: Aug. 27, 2020

(65) Prior Publication Data
US 2022/0198799 A1 Jun. 23, 2022

(30) Foreign Application Priority Data
Feb. 21, 2019 (FR) ........................ 1901772

(51) Int. Cl.
*G06V 20/40* (2022.01)
*G06V 20/52* (2022.01)
*G06V 40/20* (2022.01)

(52) U.S. Cl.
CPC .............. *G06V 20/42* (2022.01); *G06V 20/52* (2022.01); *G06V 40/23* (2022.01)

(58) Field of Classification Search
CPC ......... G06V 20/42; G06V 20/52; G06V 40/23
See application file for complete search history.

(56) References Cited

U.S. PATENT DOCUMENTS

2014/0244007 A1 8/2014 Kampman

FOREIGN PATENT DOCUMENTS

KR 1020180063777 A 6/2018

OTHER PUBLICATIONS

International Search Report for Patent Application No. PCT/EP2020/054666, Mar. 31, 2020, 2pp.

*Primary Examiner* — Mark Roz
(74) *Attorney, Agent, or Firm* — Soquel Group LLC

(57) ABSTRACT

A method for characterizing a dynamic occupancy of a space by two opposing teams of a game, including a movable sporting accessory, such as a ball, a puck or a shuttlecock, each team including at least one player. The method makes it possible to determine, for each player and for all or some of the points on the pitch, a value representative of how far in advance the player is to the point of the pitch, the representative value being computed by a comparison between the duration of movement of the player to the point of the pitch and the duration of movement of a distinct player and/or of the sporting accessory to the same point. A system is also provided for characterizing a dynamic occupancy of a space by two opposing teams of a game, implementing the method.

23 Claims, 8 Drawing Sheets

METHOD FOR CHARACTERIZING A DYNAMIC OCCUPANCY OF A SPACE BY TWO OPPOSING TEAMS OF A GAME AND RELATED SYSTEM

CROSS-REFERENCE TO RELATED APPLICATIONS

This application claims benefit under 35 USC § 371 of PCT Application No. PCT/EP2020/054666 entitled METHOD FOR CHARACTERIZING THE OCCUPANCY OF A SPACE IN THE FIELD OF SPORTS, TAKING INTO ACCOUNT THE MOVEMENT OF PLAYERS AND THE BALL, filed on Feb. 21, 2020 by inventors Vincent Bacot and Christophe Clanet. PCT Application No. PCT/EP2020/054666 claims priority of French Patent Application No. 19 01772, filed on Feb. 21, 2019.

FIELD OF THE INVENTION

The field of the invention is that of sports.
More precisely, the invention relates to a method for analyzing a dynamic occupancy of a space by two opposing teams of a game and related system.
The invention has application in particular in the field of team sports such as soccer, rugby, handball, basketball, hockey, baseball, volleyball or American football. The invention also has application in the field of racket sports such as tennis, badminton or squash.

BACKROUND OF THE INVENTION

From the prior art, techniques are known for analyzing and reproducing the positions of players on a sports field in order to allow a coach to analyze a phase of play, also called a sequence of play, and to improve the tactics applied by the players of a team.
For example, there are techniques to provide statistics on game phases, such as the number of passes made by a team, by analyzing the players' positions. Such a technique is described in U.S. Pat. No. 8,279,051, for example, but is restricted to a statistical analysis of each player's game without taking into account the area occupied by both teams.
In order to be able to analyze game phases, techniques have been developed such as the one described in the international patent application published under number WO 2017/106390, where a game sequence is associated with similar game sequences of other games, stored in a database, by statistical clustering methods. With this technique, it is specifically possible to obtain a prediction about the evolution of a game sequence. For example, in the context of a soccer match, it is possible to indicate a probability of scoring a goal based on the position of the player with the ball in relation to the goal and in relation to the other players' positions, specifically those of the opposing team, with regard to similar play sequences of other games.
However, this technique, based on a statistical analysis of previous game phases, has the disadvantage of allowing only a limited analysis of game phases because it is difficult to characterize the performance of a player or a team, and, with such a technique, to predict advantageous game phases that have not been played previously.
Despite these developments, there is still a need for additional information on game tactics, especially to characterize the occupancy of space by each team.

Analysis techniques have thus been developed to enable partitioning of an image of a sports field, to analyze the occupancy of the sports field by each team.
Such a technique is described in international patent application WO 03/037464, for example, where a soccer field is partitioned by using Voronoi diagrams. This partitioning of the sports field is performed by considering either one of the two teams, with or without the goalkeeper, or both teams at the same time. It should be emphasized that the number of partitions of the sports field corresponds to the number of players considered in the analysis, with each partition corresponding to the area of dominance of a given player and corresponds to the set of points closer to a player than to the other players.
The major disadvantage of this technique is that the tactical analysis is generally restricted in a binary way to an area occupied by each team, that is, each area is dominated either by one team or by the opposing team, not meeting the need for a measure of the local quality of dominance of one of the two teams.
None of the current systems can simultaneously meet all the required needs, namely to provide a technique that allows for a finer analysis of a phase of play, in particular by predicting an advantageous movement that could lead to one of the two teams scoring, for example, and to construct performance indicators that reflect this finer analysis.

SUMMARY OF THE INVENTION

The present invention aims to remedy all or part of the above-mentioned drawbacks of the state of the art.
To this end, according to a first aspect, the invention is aimed at a method for analyzing dynamic occupancy of a sports field by a plurality of movable elements, a movable element being a player of one of two opposing teams in a game or a game accessory, such as a large or small ball, a puck or a shuttlecock, with the game accessory being movable and each team comprising at least one player.
The sport may be a team sport such as soccer, handball, water polo, basketball, sports field hockey, baseball, cricket, volleyball, American football or rugby, for example.
Each team is made up of a number of players.
The sport may also be a racquet sport such as tennis, badminton or squash. In this case, each team generally consists of one or two players.
In general, the sport is codified by rules that establish the possibilities and constraints to be respected by each player in the sports field, which is generally delimited by markings.
It should be emphasized that the sports field is generally delimited and comprises a marked area. Moreover, this marked area generally divides the sports field into two halves, each team having a dedicated half of the sports field.
Depending on the rules of each sport, either each team is restricted to its own half of the sports field, which is the case when there is a net between the two halves of the sports field, or each team has the option of going into the opponent's half of the sports field.
For the sake of clarity, a "net sport" is a sport in which each team is restricted to one part of the sports field. Examples of such sports are volleyball, tennis or badminton.
A "shared sport" is understood as a sport where both teams share the same sports field. The sports field may be divided into two separate halves, as in soccer, rugby, handball or basketball, with each half allocated to one team. It should be emphasized that each team is generally free to occupy the half of the sports field allocated to the opposing team, within the rules of the sport.

However, the sports field may also not be divided into two distinct parts, as in squash.

The game accessory used during a game is either a ball, round or oval, a puck or a shuttlecock. It should be emphasized that generally only one accessory is present in the sports field, to be exchanged or contested by both teams.

The game accessory is generally played in a team sport on a sports field that generally has two scoring areas, each located on opposite sides of the sports field. Each team defends one of the scoring areas and will attempt to get the game accessory into the scoring areas defended by the opposing team, in order to score.

In a racquet or net sport, the game accessory is generally exchanged by both teams until the exchange is interrupted by a foul by either team, with the point being awarded to the team that did not commit the foul.

It should be emphasized that the term "game accessory" refers to any item that can be exchanged or played by both teams. A game accessory is generally movable and distinct from a piece of equipment that is part of a team's full kit, such as a hockey stick or baseball bat.

Furthermore, in the following description, when referring to a player of one team, the term "opposing player" will be understood as meaning a player on the other team, which will also be referred to as the "opposing team".

The method for analyzing a dynamic occupancy of the sports field comprises the steps of:
- acquiring an instantaneous position for all or some of the movable elements on the sports field at at least two distinct points in time, with the movable elements whose instantaneous position is known being called "movable elements considered";
- for each movable element, determination of an instantaneous speed vector;
- for each movable element located and for all or part of the points in the sports field, determination of a duration of movement between the instantaneous position of said movable element and said point in the sports field, depending on said instantaneous speed vector, and of a movement model associated with said movable element;
- for each movable element located and for all or part of the points in the sports field, determination of the time ahead of said movable element at said point points in the sports field, said time ahead being computed by a comparison between the duration of movement of said movable element towards said point points in the sports field and the duration of movement of at least one other movable element towards the same point;
- for all or some players, delimitation of an area in the sports field, called the area of dominance of said player, corresponding to all points in the area for which the time ahead of said player is greater than a predetermined threshold.

It is thus possible to carry out a finer game phase analysis by delimiting an area in the sports field in which a player dominates the game in relation the players of the opposing team. The predetermined threshold makes it possible to clearly delimit these advantageous areas in the sports field in which the players have a significant time ahead. For example, in the context of a soccer match, a time ahead can be considered significant when it is greater than 0.5 seconds. It should be emphasized that the predetermined threshold value may depend on the sport considered, or even on a particular choice of an individual such as a coach who wishes to analyze a game phase.

It should be emphasized that two areas of dominance of two distinct players may or may not overlap, whether they are on the same team or not, depending on the predetermined threshold value.

It should be emphasized that the analysis improves when the number of points of sports field covered by at least two areas of dominance decreases.

Advantageously, no area of dominance of one player overlaps another area of dominance of another player.

In other words, a point in the sports field can only be part of one area of dominance of one player.

Furthermore, when no player has time ahead greater than a predetermined threshold at a point in the sports field, this point is generally considered part of a so-called neutral area, where no team dominates.

The duration of a player's movement to a point in the sports field is the minimum time it can take for the player to reach this point in the sports field.

For each point in the sports field and for each movable element located, the duration of movement of the said movable element towards this point can be computed from the position and instantaneous speed vector of said movable element, at the moment considered, and from the characteristic parameters of the player, by resolving a movement model equation associated with said movable element according to one of the methods known to those skilled in the art.

It should be emphasized that the position and instantaneous speed of the movable elements are generally real data, acquired during a game.

A non-limiting example of an equation modeling a player's movement is provided by a model that can be written in the following form, with v the speed of the player under consideration, $v_{max}$ its maximum speed and r its characteristic acceleration time:

$$\frac{d\vec{v}}{dt} = \frac{\vec{v}_{max} - \vec{v}}{\tau}$$

Generally, the characteristic parameters associated with a player may specifically be maximum acceleration and maximum speed, or any other physical parameter associated with the player that allows for a racing model associated with the player.

The instantaneous speed of a player is generally computed from two instantaneous positions taken at two distinct times.

The instantaneous speed of the movable game accessory may be computed from two instantaneous positions taken at two distinct times, or determined by the speed of a player's interaction with the game accessory, such as the player hitting the game accessory.

The characteristic parameters associated with the game accessory generally depend on the type of game accessory. These parameters may comprise a maximum speed, friction coefficient, etc.

For each point in the sports field, the duration of movement of the game accessory to that point can be computed from the position and instantaneous speed vector of the game accessory at that point in time, by resolving the equation that models the game accessory's movement according to one of the methods known to the person skilled in the art. As a non-limiting example, the game accessory's movement can be modeled by considering that its movement is carried out at constant speed. Thus, when the game accessory is in close proximity to a player, that is, the positions of the game accessory and the player are identical or at a short distance from each other, less than 10 or 20 cm in the context of a soccer match, for example, the duration of movement $t_d$ of the game accessory towards a point in the sports field is obtained by the equation:

$$t_d = |x_{point} - x_{accessory}|/v_{accessory}$$

In this equation, |.| represents the Euclidean norm, $x_{accessory}$ the position of the game accessory, $x_{point}$ the position of the point considered and $v_{accessory}$ the maximum speed that can be given to the game accessory by the player.

It should be emphasized that, for convenience, the sports field is generally shown as a matrix of generally square or rectangular portions, equivalent to pixels of an image. Each portion can be shown by a point, called the point in the sports field, corresponding to the center of said portion, for example.

Moreover, when a moving element is no longer present in the sports field, its duration of movement towards any point in the sports field is determined as equal to infinity, for example, so that said moving element is not considered in the analysis.

Instantaneous acceleration can also be computed from two instantaneous speed vectors.

In specific embodiments of the invention, a player's area of dominance is delimited on an image that shows all or part of the sports field.

The image representing all or part of the sports field is generally a view perpendicular to the area. With the sports field generally being horizontal, the perpendicular view corresponds to a top view of the sports field.

However, the image representing all or part of the sports field may be oblique, in which case the sports field is in a perspective view.

It should be emphasized that the image representing all or part of the sports field may be schematic or correspond to a photo or video clip. In the case of a photo or video clip, the relative position and orientation of the sports field is generally determined in relation to the camera that acquired the image or video.

In specific embodiments of the invention, the method also comprises a step of delimiting the sports fields into three areas: an area of dominance for each team and a neutral area, a team's area of dominance comprising all areas of dominance of the players in the team, the neutral area corresponding to all points in all or part of the sports field not covered by an area of dominance of a team.

It is thus possible to establish a very fine analysis of phases in the game, which makes it possible to specifically predict a game phase favorable to one of the two opponents more efficiently, which can lead to scoring, such as a favorable goal scored, in the case of a soccer match.

In addition, the analysis makes it possible to specifically delimit neutral areas where no team dominates. These areas, not accessible by methods in the prior art, makes it possible to refine the game analysis by highlighting areas with a high risk of loss of the game accessory, for example, because two opposing players in these neutral areas are generally too close for one of them to keep the game accessory or to pass it quickly to another player in his/her team without risking the opposing player intercepting the game accessory and recovering it for his/her team. This is particularly the case in team sports with a shared sports field. It should be emphasized that these sports fields would be considered dominated by one of the two teams in the prior art, without taking into account the position of the players of the other team.

Furthermore, it is also possible to quantify the dominance of each player on each team. For team sports with a shared sports field, this dominance is characterized by determining their time ahead in relation to an opponent. The greater the time ahead, the more the player is considered to dominate the area in relation to his/her direct opponent because he/she can receive the game accessory and/or perform an action with the game accessory with a low risk of losing the game accessory or having it recovered by a player of the opposing team. For net sports, a player's dominance is quantified at each point by determining his/her time ahead in relation to the sports accessory. The greater the time ahead, the more the player is considered to dominate the sports field because he/she can prepare his/her return shot before receiving the accessory, consequently with a lower risk of committing a foul.

In summary, mapping that allows a finer characterization of the dynamic occupancy of the sports field by each opponent can be obtained. Specifically, this mapping allows the tactical analysis of the game phase to be improved by better visualizing the areas of dominance of each team.

In specific embodiments of the invention, the delimitation of each space in the mapping depends on a comparison between the time of movement of at least one player of each team.

Advantageously, the neutral area corresponds to the set of points in the sports field for which the difference between the minimum time of movement of each team is lower in absolute value than a predetermined threshold, the minimum time of movement of each team to a point in the sports field corresponding to the minimum value of the times of movement of the players of said team to that point.

In other words, the difference between the minimum time of movement of each team corresponds to the time ahead of a player in a team in relation to his/her direct opponent, that is, his/her closest opponent. The latter can intervene and retrieve the game accessory if sent into this neutral area.

In specific embodiments of the invention, the area of dominance of a player of a team corresponds to the set of points in the sports field for which said player has time ahead in relation to players in the opposing team greater than a predetermined threshold, the time ahead being equal to the difference between the time of movement of two players to the same point.

It should be emphasized that the absolute values of the predetermined thresholds for delimiting neutral areas and areas of dominance are generally equal. A non-limiting example of a threshold value is 0.1 s.

The area of dominance of a player in a team corresponds to the set of points in the sports field for which the player has time ahead in relation to the players of the opposing team greater than a predetermined threshold, the time ahead being equal to the difference in the duration of movement of two players towards the same point.

Advantageously, the points of the sports field for which another player of the same team has a lower time of movement than said player towards said points of the sports field are excluded from the area of dominance of a player in a team.

It should be emphasized that these specific embodiments of the invention are generally suitable for sports with a shared sports field, where the position of the game accessory is neither detected nor tracked.

In specific embodiments of the invention, the neutral area comprises those points on all or part of the sports field where the time of movement of the sports accessory is greater than the time of movement of at least one player of each team.

In specific embodiments of the invention, an area of dominance of a player in a team corresponds to the set of points in the sports field for which both:

the time of movement of said player to a point of said area of dominance is equal to the smallest of all times of movement of all players to that point, and the time of movement of the game accessory to the same point in said area of dominance is less than the smallest of the times of movement of the players of the other team.

In specific embodiments of the invention, the movable elements whose instantaneous positions are acquired are only those of players, the method also comprising a step of determining the instantaneous position of the game accessory as equal to the position of a player.

it is thus possible to estimate the instantaneous position of a game accessory without detecting it in the image. It should be emphasized that the game accessory may be hidden, or even worn, by a player, which is specifically the case during a rugby match.

When the instantaneous position of a game accessory is determined to be equal to the instantaneous position of a player, the instantaneous speed of the game accessory is generally different from the speed of that player, but rather corresponds to a speed induced by that player on the game accessory. This induced speed may be the speed in hitting a game accessory, for example, speed of passing, etc.

In specific embodiments of the invention, the sports field comprises two sports field portions, with the movements of each team constrained within a separate portion of the sports field, and the time ahead of a player computed in relation to the game accessory, the time ahead being equal to the difference between the time of movement of the game accessory to said point and the time of movement of said player to said point.

In specific embodiments of the invention, the time ahead of a team at a point on the portion of the sports field occupied by said team is the maximum time ahead of the players of said team.

In specific embodiments of the invention, the area of dominance of a team in the portion of the sports field occupied by the opposing team corresponds to the set of points in said portion of the sports field for which the time ahead of the game accessory is greater than a predetermined threshold, the time ahead of the game accessory being equal to the difference between the smallest of the times of movement of the players of the opposing team and the time of movement of the game accessory to said point.

In specific embodiments of the invention, the delimitation of each area in the mapping depends on a comparison between the time of movement of at least one player and a time of movement of the game accessory, the time of movement of the game accessory being determined from a previously acquired instantaneous position of the game accessory and a movement model associated with said game accessory.

In this way, the delimitation of areas of dominance and neutral areas can be refined by taking into account the instantaneous position of the game accessory.

In other specific embodiments of the invention, the delimitation of each area in the mapping depends on a comparison between the time of movement of at least one player and a time of movement of the game accessory, the time of movement of the game accessory being determined by assuming its position as equal to the instantaneous position of a player distinct from the at least one player.

Is thus possible to perform the analysis without knowing the instantaneous position of the game accessory, but by considering a hypothetical position of the game accessory as equal to a player's position. This is particularly useful when the game accessory cannot be detected or tracked in a video stream.

In specific embodiments of the invention, the neutral area corresponds to points where the time of movement of the game accessory is greater than the time of movement of at least one player on each team.

An area of dominance of a player in a team then corresponds to the set of points in the sports field for which both:

the time of movement of said player to a point in said area of dominance is equal to the smallest of all times of movement of all players to that point, and the time of movement of the game accessory to the same point of said area of dominance is less than the smallest time of movement of players of the other team.

These specific embodiments of the invention are generally suitable for shared sports fields, where the position of the ball is detected and tracked.

In other specific embodiments of the invention, an area of dominance of a player of a team in his/her portion of the sports field corresponds to the set of points in his portion of the sports field for which both:

the time of movement of said player to a point of said area of dominance is equal to the smallest of all times of movement of all players in said part of the sports field to that point, and the time of movement of the game accessory to the same point of said area of dominance is greater than that of said player.

An area of dominance of a player in a team in the opposite part of the sports field then corresponds to the set of points in the opposite part of the sports field for which the time of movement of the game accessory, from the position of said player to the point of said area of dominance, is less than the smallest of all times of movement of all players in the opposite part of the sports field. The area of dominance of a team in the opposite part of the sports field is then the sum of the areas of dominance of the players of a team in the opposite part of the sports field.

The neutral area of a part of the sports field occupied by a team then corresponds to the set of points of the said part of the sports field for which the duration of movement of the game accessory towards this point is similar to the smallest of durations of movement of the players of the team occupying this part of the sports field towards this point, that is, the absolute value of the difference between the two minimum durations is lower than a predetermined threshold.

In other words, the neutral area corresponds to the points where the minimum time for the opposing team to send the game accessory to that point is close to the minimum time of movement of the players of the team occupying that part of the sports field. A predetermined maximum difference threshold between the two times makes it possible to determine whether these times are close or not. A non-limiting example threshold is 0.1 s.

In specific embodiments of the invention, the duration of movement of the game accessory towards a point of a part of the sports field considered to define the area of dominance of a player of the team occupying said part of the sports field, to define the area of dominance of the opposing team and to define the neutral area, is the smallest of the durations of movement of the game accessory from one of the positions of the opposing players towards this point.

It is thus possible to perform the analysis without knowing the instantaneous position of the game accessory, but by considering a hypothetical position of the game accessory as equal to the position of an opposing player, with this opposing player being chosen as the one associated with the smallest time to move the game accessory. This is especially useful when the game accessory cannot be detected or tracked in a video stream.

It should be emphasized that these specific embodiments of the invention are generally suitable for net sports.

Advantageously, the area of dominance of a team corresponds to the set of areas of dominance of the players of said team.

In particular embodiments of the invention, the method also comprises a step of determining a value representing the dominance of a player at a point of the sports field, said value being equal to the difference between the smallest of the times of movement of the players of the other team towards said point and the time of movement of said player towards said point. These embodiments are generally suitable for shared sports fields, where the game accessory cannot be detected or tracked.

In specific embodiments of the invention, the method also includes a step of determining a value representing a player's dominance at a point in the sports field, said value being equal to the minimum of:
  the difference between the smallest time of movement of players of the other team to said point and the time of movement of said player to said point, on the one hand;
  the difference between the smallest time of movement of players of the other team to said point and the time of movement of the game accessory to said point on, the other hand.

Advantageously, in these specific embodiments, the value representing dominance is set to zero for the neutral area.

These specific embodiments of the invention are generally suitable for shared sports fields, where the game accessory can be detected and tracked.

In other specific embodiments of the invention, the method also includes a step of determining a value representing a player's dominance at a point on his/her portion of the sports field, said value being equal to the difference between the duration of movement of the game accessory to said point and the duration of movement of said player to said point.

Advantageously, in these specific embodiments, the value representing the dominance of a team at a point on its portion of the sports field corresponds to the maximum of the values representing the dominance of the players on that team.

In these specific embodiments, the method also includes a step of determining a value representing the dominance of a team at a point of the part of the sports field occupied by the opposing team, said value being equal to the difference between the smallest of the times of movement of the opposing players to said point and the time of movement of the game accessory to said point. It should be emphasized here that the values representing the dominance of one team and of the other in the same part of the sports field oppose each other. These embodiments are generally suitable for net sports.

These specific embodiments of the invention are generally suitable for net sports.

In specific embodiments of the invention, the duration of movement of the game accessory to a point on a portion of the sports field considered, to define the value representing the dominance of a player in the team or of a team occupying said portion of the sports field, or to define the value representing the opposing team, is the smallest of the durations of movement of the game accessory from any of the positions of the opposing players to that point. It is thus possible to perform the analysis without knowing the instantaneous position of the game accessory, but by considering a hypothetical position of the game accessory as equal to the position of an opposing player, this opposing player being chosen as the one associated with the smallest time of movement of the game accessory. This is particularly useful when the game accessory cannot be detected or tracked in a video stream.

In specific embodiments of the invention, the method also includes a step of determining a value representing the dominance of a player at a point on the opposing side of the sports field, said value being equal to the difference between the smallest of the times of movement of the players of the team and the time of movement of the game accessory from the position of said player to said point.

These specific embodiments of the invention are generally suitable for net sports.

In specific embodiments of the invention, the method includes a step of determining a color intensity, depending on player dominance.

For example, each team's dominance areas may be subdivided into areas of greater dominance and lesser dominance. Generally, the greater dominance areas are darker in intensity than the lesser dominance areas, creating a color gradient between a neutral area and a high dominance area.

It should be emphasized that the quality of dominance can be computed at any point in the sports field and that the dominance values can be shown as a continuous and differentiable surface.

Generally, each opponent is shown in a different color (e.g. red and blue). Neutral areas are also shown with another color (e.g. white).

In specific embodiments of the invention, the mapping generation is performed in real time.

It should be emphasized that the mapping generation is generally done in real time in relation to the broadcasting of the video stream, which may be broadcast live or delayed.

Real time is understood as processing carried out almost immediately, generally less than a few tenths of a second, so that the mapping can be synchronized with the image of the video stream displayed almost directly on the screen.

In specific embodiments of the invention, the method also comprises a step of acquiring a video stream by at least one camera that covers all or part of the sports field, the step of acquiring the instantaneous position of the game accessory comprises a sub step of analyzing the video stream to determine said instantaneous position.

Preferably, each camera is fixed and covers all or part of the sports field.

Advantageously, all of the cameras cover the entire sports field.

In specific embodiments of the invention, the step of acquiring the instantaneous position of each player comprises a sub step of analyzing the video stream to determine said instantaneous position.

In specific embodiments of the invention, the mapping is synchronized and overlaid on the video stream.

It is thus possible to see an augmented image of the sports field in real time, in other words an image of the sports field in which the areas of dominance of each team or even the neutral spaces, are overlaid. Additional information, such as values representing the quality of dominance within the dominance areas, can also be overlaid on the image.

In specific embodiments of the invention, the method includes a step of tracking any or all of the players and/or game accessory in the video stream.

In this way, the instantaneous position of any or all of the players and/or the game accessory can be determined in the video stream.

In specific embodiments of the invention, the step of determining the position of each player in the sports field comprises a sub step of analyzing a signal emitted by a tracker attached to said player and received by at least one terminal located near the sports field.

Preferably, the signals transmitted by the trackers are received by at least three terminals located in the vicinity of the sports field.

In specific embodiments of the invention, the method also comprises a step of determining at least one quantitative indicator of a qualitative characteristic of a player selected from:
- a value representing the player's dominance in at least one part of the sports field, computed from the dominance area characteristics recorded during a match;
- quality of passing the game accessory;
- quality of individual dominance of a portion of the sports field;
- a value representing the pressure undergone by said player;
- a quality of striking the game accessory;
- the rate of unforced errors.

In specific embodiments of the invention, the method also comprises a step of determining at least one quantitative indicator of a qualitative characteristic of a team, constructed by aggregating the individual indicators of its players.

In specific embodiments of the invention, these quantitative performance indicators may be computed and displayed and/or recorded without necessarily displaying the associated dynamic dominance mappings.

In specific embodiments of the invention, the method further comprises the steps of:
- displaying the video stream on which at least one player tracking indicator is superimposed, in real time, and
- an operator repositioning the tracking indicator.

A tracking error can thus be corrected quickly. Indeed, it should be emphasized that since tracking a player is generally based on tracking the contour of the player's image in the video stream, the contour tracking happens to switch to another player when the images of the two players overlap in the video stream.

According to a second aspect, the invention is directed to a system for analyzing a dynamic occupancy of a sports field by two opposing teams of a game, implementing the method for generating a mapping according to any of the preceding embodiments.

The system for analyzing a dynamic occupancy of the sports field specifically comprises:
- means for acquiring the instantaneous position of each player in the sports field;
- means for acquiring the instantaneous position of the game accessory in the sports field;
- means for data processing by computer, comprising a processor and a computer memory;
- means for graphically displaying the generated map and associated indicators.

In specific embodiments of the invention, the means for acquiring the instantaneous position comprises at least one camera that acquires a video stream covering all or part of the sports field.

In specific embodiments of the invention, the means for acquiring the instantaneous position of each player and/or of the game accessory comprises at least one tracker and at least one terminal, for receiving a signal emitted by said tracker.

Advantageously, at least one tracker can be attached to a player and/or to the game accessory. A tracker can also be used to determine the limits of the sports field.

Preferably, the means of acquisition comprises at least three receiving terminals.

In specific embodiments of the invention, the means for acquiring the instantaneous position of the game accessory comprises at least one camera that acquires all or part of the sports field.

Advantageously, the set of cameras for acquiring the instantaneous position of each player is identical to the set of cameras for acquiring the instantaneous position of the game accessory.

In other words, the video stream acquired by the camera(s) is used to acquire both the instantaneous positions of each player and the game accessory in the sports field.

In specific embodiments of the invention, an alert is displayed in real time if a particular action is detected, such as when a sports field is dominated by the opponent in the penalty area in soccer, allowing the team to better monitor its management of the area. For example, it allows the team to be informed of an opportunity for favorable action before it occurs.

In specific embodiments of the invention, the system also comprises a means of recording acquired data and of modification, by a user, of all or part of the recorded data of instantaneous positions and/or speeds of the movable elements.

It is thus possible to modify recorded parameters in order to improve game tactics. For example, the speed of at least one player can be modified, in the norm and/or in the orientation, in order to see the impact on the current game phase. This makes it possible to answer a question such as: "what would have been the dynamic dominance in this area if . . . ?" (what would have been the dynamic dominance in this area if one of the players had had an instantaneous speed ten times slower, for example)

BRIEF DESCRIPTION OF THE DRAWINGS

Further advantages, objects and particular characteristics of the present invention will be apparent from the following non-limiting description of at least one specific embodiment of the devices and methods that are the objects of the present invention, with reference to the appended drawings, in which.

DETAILED DESCRIPTION OF THE INVENTION

The present description is given as non-limiting, with each characteristic of one embodiment capable of being combined advantageously with any other characteristic of any other embodiment.

It is emphasized that the Figures are not to scale, at this time.

Example of a Specific Embodiment

Figure 1:
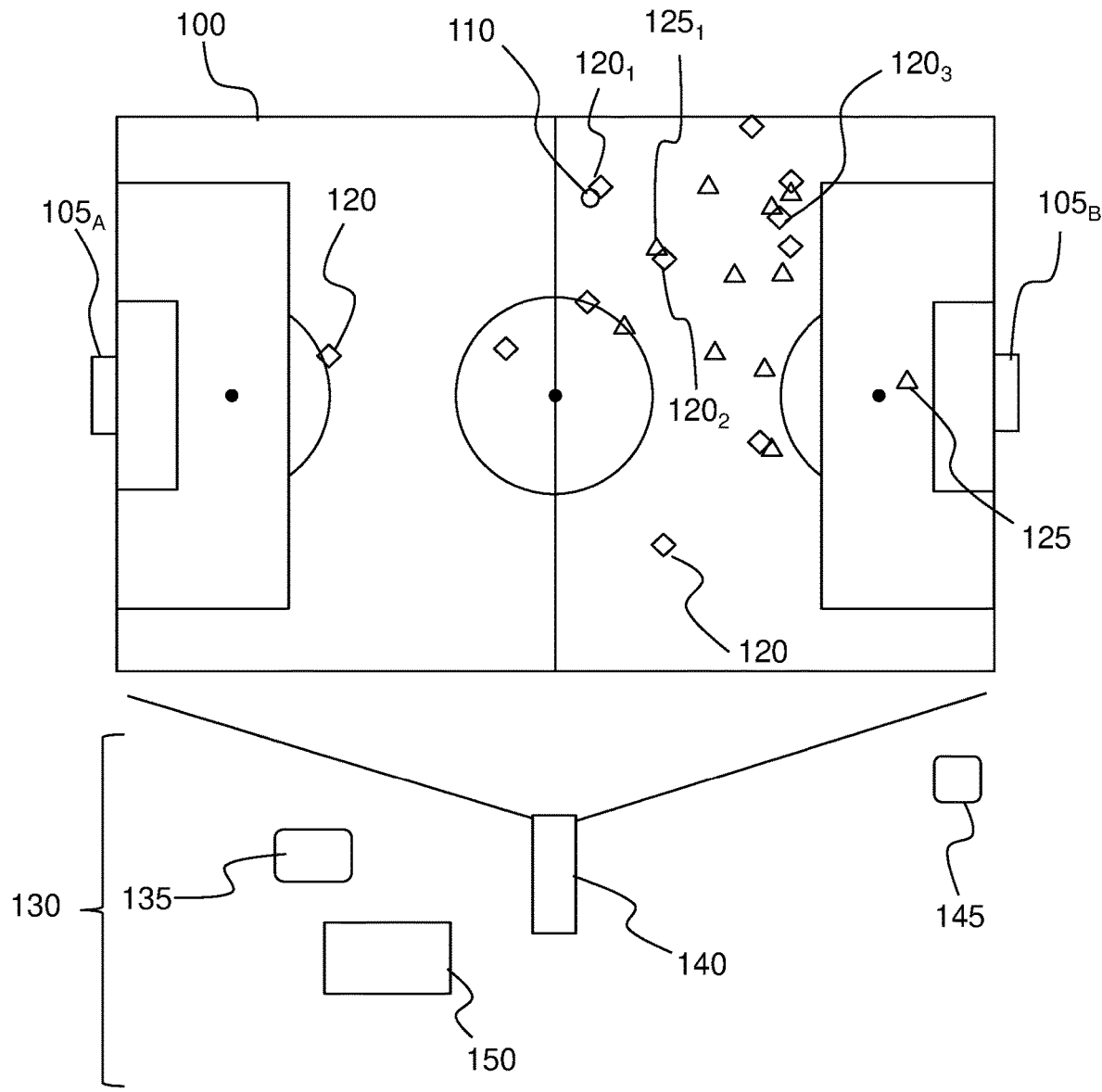
FIG. 1 is an overall diagram representing a system for analyzing the dynamic occupancy of a sports field by two opposing teams in a soccer game.

FIG. 1 shows a schematic of a soccer field 100 as viewed from above, on which two opposing teams compete against each other and compete for a moving game accessory, a soccer ball 110 in this example. Each team, comprising eleven players, has the objective of kicking the ball 110 into one of the two scoring areas 105, each located at an opposite end of the sports field 100.

It should be emphasized that soccer is played entirely within the outer marking line of the sports field 100. As soon as the ball 110 leaves the marking of the sports field 100, the game is interrupted.

For the sake of clarity in FIG. 1, the players 120 of one of the two teams, hereafter called team A, are shown as diamonds, defending the scoring area $105_A$ located in FIG. 1 on the left lateral edge of the sports field 100, while the players 125 of the other team, hereafter called team B, corresponding to the opposing team, are shown as triangles.

The objective of the team A players 120 is to send the ball 110 into the scoring area $105_B$ located on the right lateral edge of the sports field 100 shown in FIG. 1 and defended by the team B players 125. Conversely, the team B players 125 have the objective of sending the ball 110 into the scoring area $105_A$ defended by team A. Each time the ball 110 enters completely into one of the scoring areas 105, the team not having to defend that scoring area scores.

In order to analyze at least one phase of the game and with a view to improving each team's game tactics, a system 130 for analyzing a dynamic occupancy of the sports field 100 according to the invention is used.

It should be emphasized that the sports field 100, for the analysis, is subdivided into a plurality of generally square portions (not shown in FIG. 1), which may also be referred to as pixels. The smaller the size of the portions of the sports field 100, the finer the analysis of the occupancy of the sports field 100. Each portion of the sports field 100 is shown as a point, which generally corresponds to the center of the portion. Hereafter, a point will be understood as the center of a portion of the sports field 100.

The analysis system 130 specifically comprises the means for acquiring the instantaneous position of each player 120 and 125 and of the ball 110 in the sports field 100. In this non-limiting example of the invention, these means for acquiring include a camera 140 to acquire a video stream covering the entire sports field 100. It should be emphasized that a stream is a succession of still images, generally taken at a rate of between twenty-five images per second and one hundred images per second.

In order to minimize the processing of the images of the video stream, the camera 140 is advantageously fixed.

In variants of this specific embodiment of the invention, the means for acquiring the instantaneous position of each player 120 and 125 and of the ball 110 in the sports field 100 comprise a plurality of fixed cameras, each acquiring a video stream covering a portion of the sports field 100. The entire sports field 100 is thus covered by a plurality of cameras.

The players' positions, obtained by each camera, are then collated. The use of a plurality of cameras generally provides more accurate positions of the players in the sports field 100, with determination of the position depending on the resolution of the image obtained by the camera.

The images acquired by the camera 140 are processed by computer processing means 135 of the analysis system 130 in order to determine the instantaneous position of each player 120 and 125 and/or the ball 110 in the sports field 100.

To this end, the computer processing means specifically comprises a processor and a computer memory.

In order to improve or determine the instantaneous position of all or part of the players 120 and 125 in the sports field 100, the analysis system 130 may also comprise a terminal 145 for receiving a presence signal emitted by at least one tracker (not shown in FIG. 1) attached to all or part of the players 120 and 125, and/or the ball 110.

These trackers may be specific GPS-type geolocation trackers that emit a presence signal at regular intervals, transmitting an identification associated with the player to which the tracker is attached and the geographical position of the tracker at the time of emission of the presence signal.

In variations of this specific embodiment of the invention, the analysis system 130 comprises three receiving terminals in order to locate the position of a tracker emitting a presence signal by triangulation or trilateration.

To this end, the presence signal emitted by each tracker can advantageously be modulated according to the UWB ("Ultra-Wide Band") technique in order to reduce errors in measuring the propagation time of the presence signal received by the receiving terminals.

It should be emphasized that the acquisition of the instantaneous position of the players 120 and 125 in the sports field 100 can be performed thanks to the presence of trackers attached to the players 120 and 125 without processing the images acquired by the camera 140. However, acquisition of the instantaneous position by processing the images may be advantageous when at least one player of one of the opponents present in the sports field 100 is not wearing a tracker.

The computer memory specifically stores a computer program comprising instructions to implement a method, according to the invention, for analyzing the dynamic occupancy of the sports field 100 by the two opposing teams, in order to generate a mapping representing this occupancy and associated performance indicators from the instantaneous position of the players 120 and 125 and the ball 110 in the sports field 100.

The mapping generated and associated performance indicators are then displayed on a screen 150 of the means of display of the analysis system 130.

The mapping provides a visual indication of the quality of dominance at any point in the sports field by either team, or by none. The sports field can thus be subdivided into at least three areas, including an area of dominance for each team and a neutral area where no team is dominant.

Quality of dominance at a point is understood as a value representing the dominance of a team at this point. This value is computed in relation to the time ahead of a player of the team in relation to the closest player of the opposite team.

Depending on the time ahead, each point of the sports field can be associated with an area of dominance of one of the teams if the time ahead of one of the teams is significant, that is, higher than a predetermined threshold value (0.1 s, for example). In the case where no player of a team has a significant time ahead in relation the other players at this point, that is, the maximum time ahead is lower than the threshold value, the point is considered associated with the neutral area.

Thanks to this astute delimitation of the sports field, it is thus possible to obtain a fine analysis of each game phase in order to improve the tactics of at least one team.

The specific performance indicators may be:
the individual quality of a player or team dominating the whole sports field or a specific area of the sports field (e.g. the area close to scoring) at one moment, estimated by the portion of this area dominated by the said player or team, for example, as well as by the characteristic value of the quality of dominance in this area;
the individual quality of a player or team of dominating a specific area of the sports field (e.g. the area close to scoring) over part of the match, estimated by the number of game sequences and total time during which a portion of a specific area has been dominated by said player or team, for example;
the quality of completion of a pass or of all the passes of a player or a team, associated with the quality of the dominance at the end point of the pass;
the possible passing opportunities at each moment during all or part of the match;
a value representing the pressure exerted on the ball carrier.

Figure 2:
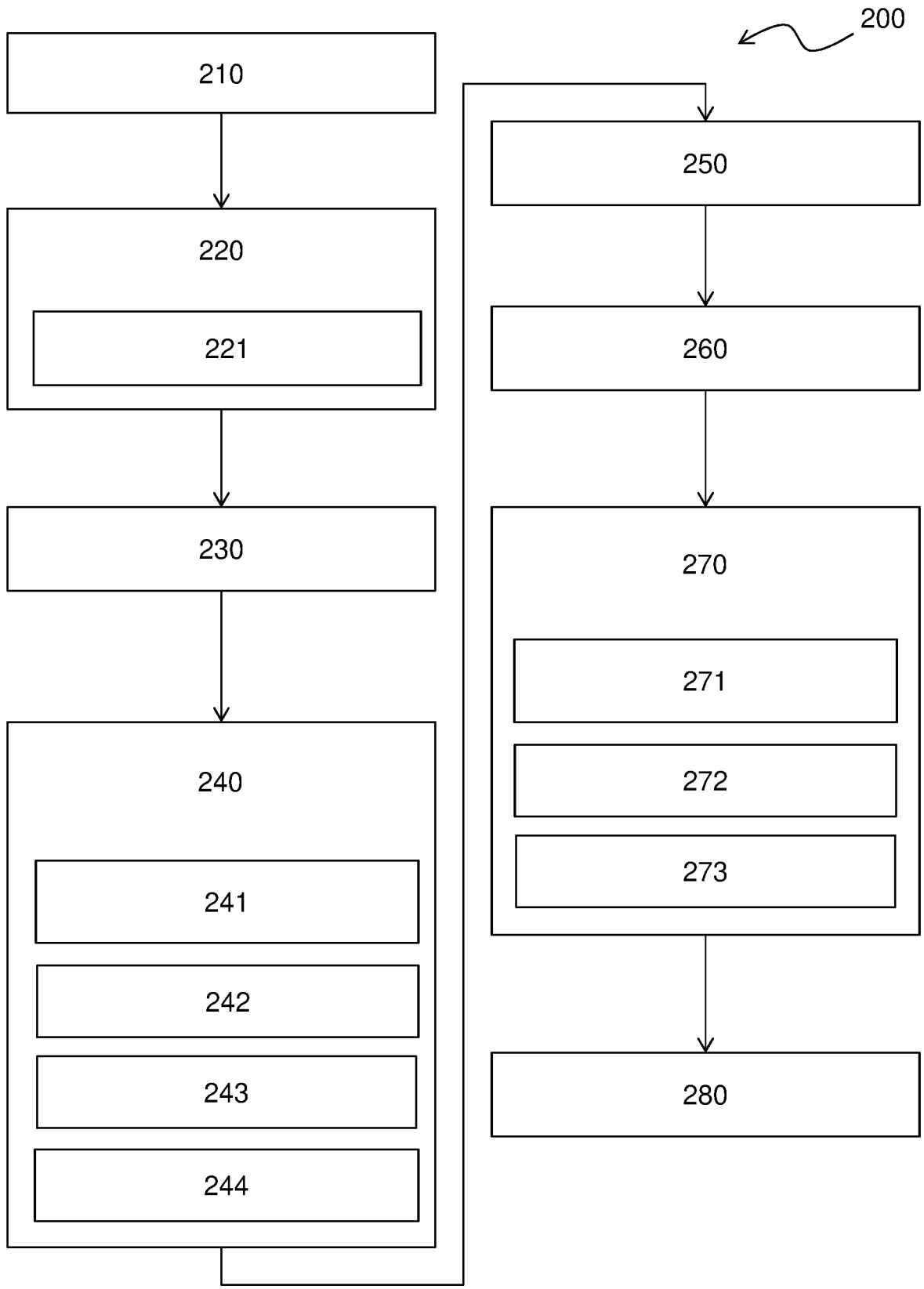
FIG. 2 is a synoptic diagram of an analysis method implemented by the analysis system of FIG. 1.

FIG. 2 shows the method 200 for analyzing the dynamic occupancy of the sports field according to the invention, in the form of a block diagram.

In this non-limiting example of the invention, the method 200 comprises a step 210 of acquiring a video stream by the camera 140.

The video stream acquired is then processed during the step 220 of acquiring the instantaneous position of the ball 110 on the sports field 100.

To this end, the step 220 includes a sub step 221 of analyzing the video stream, to determine the instantaneous position of the ball 110. This analysis is specifically performed by detecting the ball 110 in a frame of the video stream and tracking the ball 110 in successive frames of the video stream. The tracking is generally carried out by means of a contour that follows the shape of the ball 110, or by any other technique known to the person skilled in the art.

It should be emphasized that when the ball 110 is located outside the sports field 100, with play stopped, the present analysis is generally suspended until the ball 110 returns to the sports field 100 so that play can resume.

From the instantaneous position of the ball 110 in the sports field 100, a minimum time of movement of the ball 110 from its instantaneous position to any point in the sports field 100 can be determined. To perform this calculation, a maximum speed of the ball 110 is generally considered. The value of the maximum speed of the ball 110 represents the speed generally seen during a soccer match. It is a parameter that can be determined at the beginning of the analysis by an operator or adapted during the analysis according to the maximum speed recorded during the game. The speed of the ball 110 can specifically be determined from successive positions of the ball 110 in the video stream images.

Determination of a minimum duration of movement of the ball 110 is performed during step 230 of the method 200, for all or some of the points in the sports field.

Furthermore, the video stream acquired by the camera 140 may also be processed during the step 240 of acquiring the instantaneous position of each player 120 and 125 in the sports field 100.

To this end, the step 240 comprises a sub step 241 of analyzing the video stream to determine the instantaneous position of each player 120 and 125. This analysis detects the presence of the players 120 and 125 and tracks them in successive frames of the video stream. As with tracking the ball 110, the tracking of each player is generally performed by means of a contour that follows the shape of the player or by any other technique known to the person skilled in the art.

It should be emphasized that the detection does not generally recognize the player, since it is done in a general way so that the tracking can be done in real time.

In order to compensate for tracking errors, when two contours overlap, for example, the step 240 may also include a sub step 242, allowing an operator to intervene and correct the player tracking displayed on a control screen. For this purpose, the control screen displays the video stream acquired by the camera 140 on which one tracking indicator per player is superimposed, the operator being able to reposition at least one indicator, if necessary.

It should be emphasized that a third party, not belonging to either team, namely a referee, is generally also present on the sports field 100. This third party is advantageously not considered in the present dynamic sports field occupancy analysis. The operator can also stop tracking of this third party in the video stream images.

In the event that the third party is carrying a tracker, the resulting position associated with the tracker is not considered in the analysis.

Step 240 may also include a sub step 243 of acquiring signals emitted by the trackers attached to the players.

From the data from the camera images and/or player trackers, the instantaneous position of each player 120 and 125 in the sports field is determined in a sub step 244. It should be emphasized that when a player is not present in the image or is located off the sports field so that he/she is no longer participating in the game, he/she is indicated as "off the field" and is not considered in the rest of the analysis.

For each player present in the sports field 100, an instantaneous speed vector is determined during a step 250 of the method 200 from two successive positions of said player. This vector comprises a direction, corresponding to the direction of movement of said player and a norm, corresponding to the instantaneous speed of said player.

In addition, the duration of movement between the instantaneous position of each player and each point in the sports field is determined during a step 260 of the method 200, depending on the instantaneous speed vector and physical parameters associated with each player, such as a maximum acceleration and speed. When a player is considered "off the field," the associated time of movement to any point in the sports field is equal to infinity, in this non-limiting example of the invention.

Figure 4:
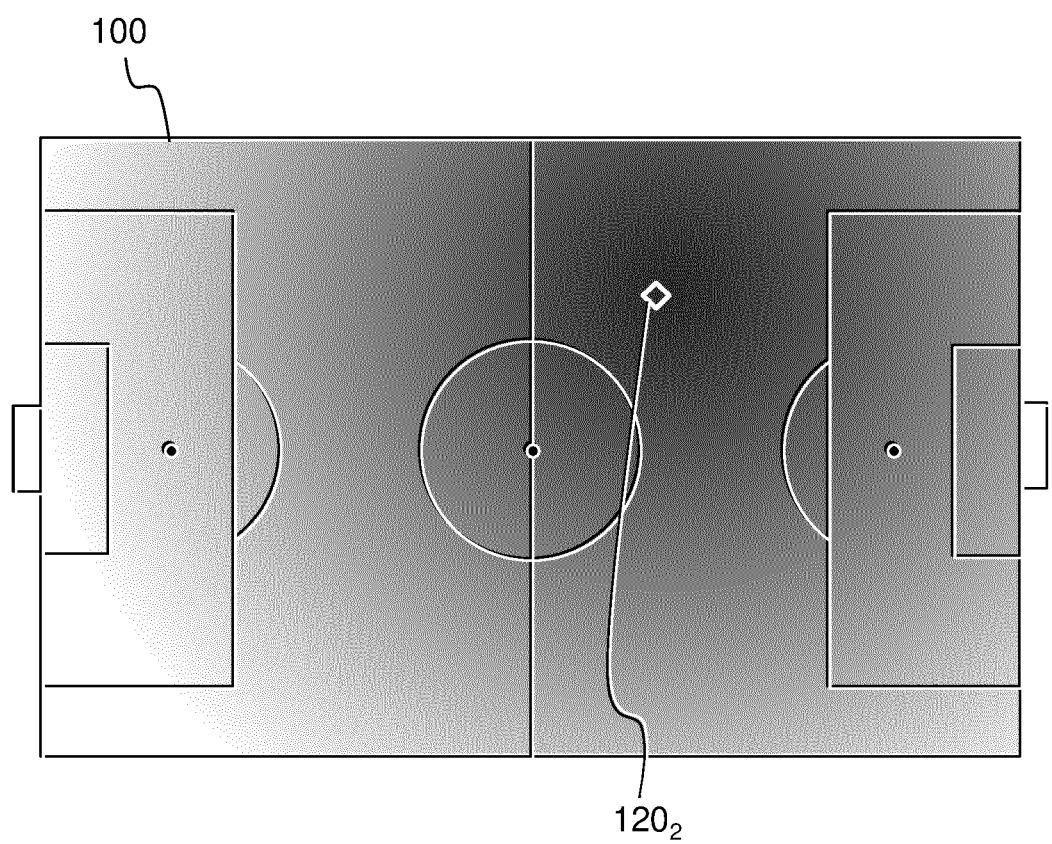
FIG. 4 is a mapping of the individual times of movement of one of the players in the sports field, obtained during the method of FIG. 2, the times of movement being used to obtain the mapping of FIG. 3A.

An example of mapping the time of movement of the player $120_2$ in the sports field 100 is shown in FIG. 4.

For each point in the sports field 100, a time ahead is computed for each player in a step 265 by comparing the time of movement of the players to the same point. The time ahead at a point of one player relative to another player is equal to the difference between the times of movement of the two players to the same point.

The method then comprises a step 270 of delimiting the sports field 100 into three areas, including an area of dominance for each team and a neutral area where no team is dominant.

The area of dominance for each team is computed in a sub step 271 of step 270. The area of dominance of a player in a team corresponds to the set of points in the sports field 100 for which the time ahead of said player is greater than a predetermined threshold.

Advantageously, the area of dominance of a player in a team corresponds to the set of points in the sports field 100 for which both:
- the time of movement of said player to a point of said dominance sports field is equal to the smallest of all times of movement of all players to that point, and
- the time of movement of the game accessory to the same point of said area of dominance is less than the smallest of the times of movement of the players of the other team.

In other words, the time ahead of a player at a point is computed in relation to the other players, specifically the players of the other team, also taking into account the time of movement of the game accessory at that point.

It should be emphasized that the area of dominance of a team corresponds to the set of areas of dominance associated with the players of this team.

For the mapping display, the area of dominance associated with the team of players 120 is associated with the color blue for example. While a separate color, red for example, is associated with the area of dominance associated with the team of players 125.

Advantageously, the intensity of the color of the dots in each area of dominance is computed based on the player's dominance in a sub step 272 of step 270. The color is more intense when one team's player has significant time ahead of players on the other team, in other words, when the time of movement of one team's player is noticeably less than that of the players on the other team.

For example, a color intensity scale comprising a hundred shades of blue is associated with a time ahead range of between 0 and 3 seconds (s). This range is thus divided into a hundred time ahead categories (between 0 s and 0.03 s, between 0.03 s and 0.06 s, etc.). The scale goes from the lightest (almost white) for the smallest time ahead category, to the darkest for the highest time ahead category. The pixel color value, if the time ahead is less than or equal to 3 s, is obtained at a point in the graphical mapping representation at the associated intensity shade in the scale. If the time ahead is greater than 3 s, the pixel is assigned the maximum intensity in the scale.

Step 270 also comprises a sub step 273 of determining a neutral area that corresponds to points where the minimum time of movement of the game accessory is greater than the time of movement of at least one player on each team.

It should be emphasized that a player on a team could have little or no area of dominance, as long as the area surrounding that player is considered part of the neutral area.

The color white is generally associated with the neutral area(s) in the mapping.

The mapping is then displayed on a display screen in real time during a step 280 of the method 200, to a coach of one of the two teams, for example.

Advantageously, the mapping is synchronized and superimposed on the video stream acquired by the camera 140.

Performance indicators can also be displayed in real time at the same time as the mapping.

It should be emphasized that the positioning data of the players of each team and the game accessory, as well as the mappings displayed at each moment and the performance indicators, can advantageously be saved for analysis or viewing after the game.

Figure 3:
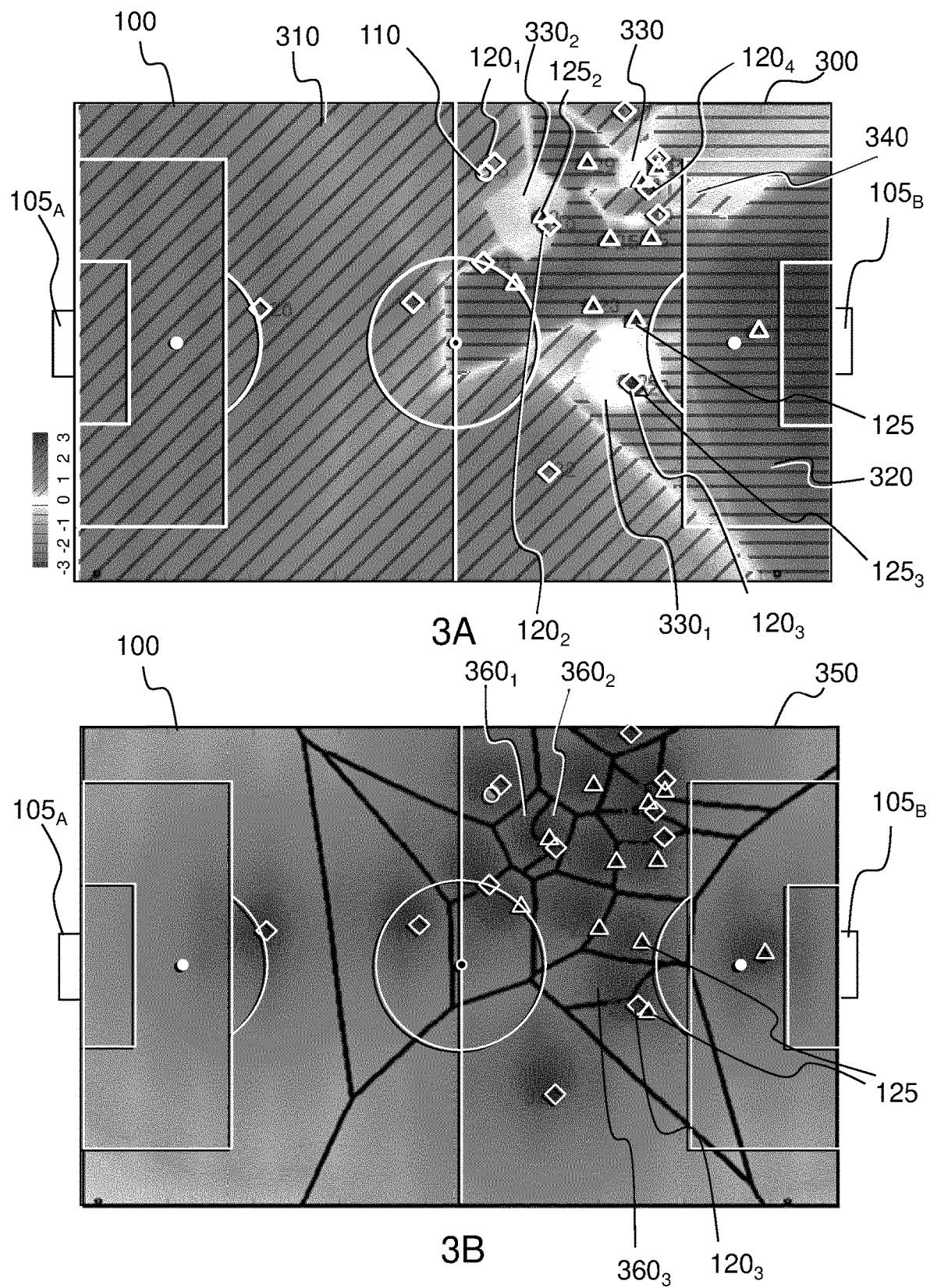
FIG. 3 is a comparison of two mappings obtained either by the analysis method of FIG. 2 (FIG. 3A) or by the methods of the prior art (FIG. 3B)

FIG. 3 shows a comparative example of a mapping 300 obtained by the analysis method 200 (FIG. 3A) and a mapping 350 obtained by methods of the prior art (FIG. 3B). The mappings 300 and 350 are computed over the game phase shown in FIG. 1.

The mapping 350 is partitioned into partitions 360 via a method of the prior art, while the color intensity shows the time of movement of the different players.

In the mapping 300, the team A of players 120 protecting the scoring area $105_A$ and seeking to kick the ball 110 into the scoring area $105_B$ is in a dominant position over most of the sports field 100. team A's area of dominance 310 is shown by a thick hatching at a 45° angle in relation to an edge of the sports field 100.

team B of players 125 protecting the scoring area $105_B$ is in a defensive position in which all the players 125 are on the right half of the sports field in FIG. 3A. team B's area of dominance 320 is shown on the mapping 300 by fine hatching parallel to the longitudinal edge of the sports field 100.

On the mapping 300 obtained by the analysis method 200, there are neutral areas 330, where no team dominates.

These neutral areas 330 generally correspond to a position very close to at least two opposing players, in other words at least one player from each team. These neutral areas, such as the area $330_2$, correspond to an area where no opponent can dominate because the difference between the times of movement of the two close players is very small, less than the predetermined threshold. It should be emphasized the area $330_2$ corresponds to two partitions $360_1$ and $360_2$ in the mapping 350 obtained with methods of the prior art, in which the partition $360_1$ is dominated by team A, while the partition $360_2$ is dominated by team B. In addition, it should also be emphasized that the intensity in the mapping 350 does not depend on the position of the opposing players, but simply on the time of movement of the player associated with the partition.

In particular, if the player $120_1$ sends the ball 110 into the area $330_2$, thinking that the player $120_2$ specifically would be dominant there, it cannot be ruled out that his/her opponent $125_2$ will put pressure on the player $120_2$ and recover the ball, since the arrival time ahead there of the former will be almost zero due to the proximity of the player $125_2$.

In other words, the neutral areas 330 where no team dominates appear in the mapping 300 obtained by the analysis method 200, whereas an area of dominance associated with a player of one of the two teams is seen in the mapping 350 obtained with methods of the prior art.

In particular, if the player $120_1$ sends the ball 110 into the area $330_1$, thinking that the player $120_3$ would be dominant there, it cannot be ruled out that his/her opponent $125_3$ could recover the ball 110.

In the mapping 350, it appears that the partition $360_3$ between two players 125 is dominated by team A's player $120_3$. While in the mapping 300, this partition $360_3$ corresponds to a neutral area $330_1$ due to the significant distance of the ball 110.

Furthermore, the mapping 300 shows an area 340, of the area of dominance 310, very favorable to team A. This area of dominance 340 of the player $120_4$ corresponds to the potential game action where the player $120_1$ sends the ball towards the player $120_4$. In other words, the player $120_1$ passes the ball 110 to the player $120_4$ in his/her play.

If the pass is completed correctly by the player $120_1$, then the player $120_4$ may be in a favorable position with the ball 110 in the area of dominance 340 where he/she may attempt to kick the ball 110 into the scoring area $105_B$, which may result in team A scoring.

It should be emphasized that the mapping 300 makes it possible to appreciate this very favorable situation for team A, in that it reveals that the area 340 is specifically dominated by the player $120_4$, which is not visible on the mapping 350 obtained with methods of the prior art, because the methods of the prior art are only based on the instantaneous position and speed of each player 120 and 125, independently of the other team, that is, without taking into account the instantaneous position and/or possible trajectories of the opponents and/or the ball 110.

In addition, the mapping 300 also shows neutral areas where no team is dominant, due to the distance of the ball and/or proximity of an opponent.

It should be emphasized that the mapping 300 representing the sports field 100 is partitioned entirely into areas that correspond either to an area of dominance by one of the two teams or to a neutral area.

The analysis method 200 thus makes it possible to quantitatively characterize the dynamic occupancy of the sports field 100, making relevant predictions of all physically possible movements.

In summary, the method 200 makes it possible to reveal the existence of neutral areas caused by the distance of the ball and to highlight a dynamic advantage of a player of a team over his direct opponent, as is the case of player $120_4$ specifically.

From the analysis performed by the method 200, it is also possible to determine a certain number of indicators that characterize each player, such as the quality of the pass performed by a given player, for example, by taking into account the available areas of dominance of each team player, the quality of the dominance in each area and the neutral areas.

Figure 5:
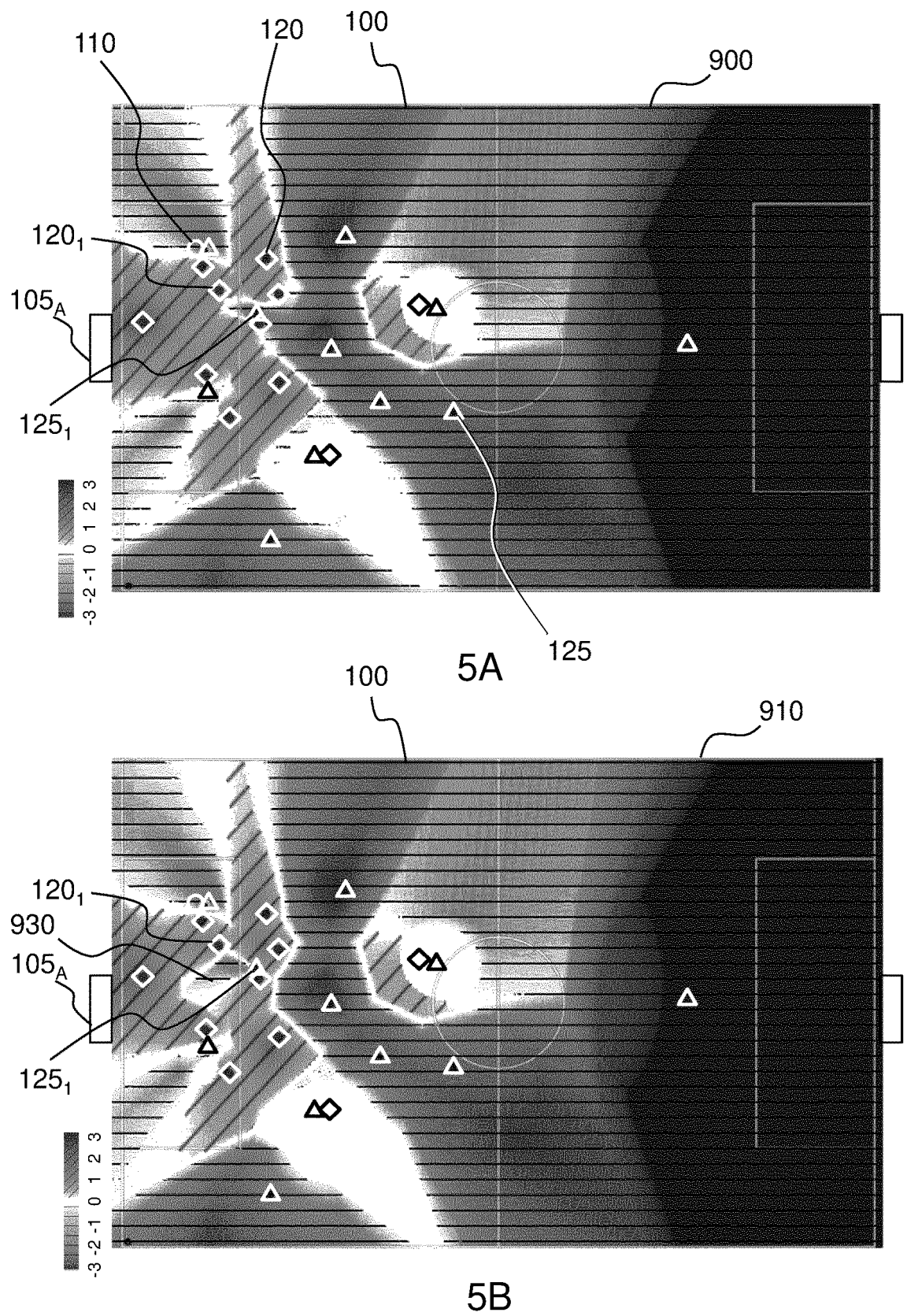
FIG. 5 is a comparison of two mappings obtained by the analysis method of FIG. 2, in order to analyze the evolution of tactics according to a given scenario, the mapping of FIG. 5A being computed from the instantaneous positions and speeds acquired, the mapping of FIG. 5B being computed from the instantaneous positions and speeds acquired while taking a modification of a player's instantaneous speed into account.

FIG. 5 is a comparison of two mappings obtained by the analysis method 200. The mapping 900 in FIG. 5A is computed from the instantaneous positions and instantaneous speeds of the players 120 and 125, acquired at a given time during a game phase. While the mapping 910 of FIG. 5B is computed from the same instantaneous positions and instantaneous speeds of the players 120 and 125, acquired at the same instant, except that the speed of the player $125_1$ has been modified (from 3 km/h to 30 km/h) a posteriori by an individual such as the coach, through a control interface, in order to see the impact on the game phase.

An area of dominance 930 favorable to team B thus appears in FIG. 9B where player $125_1$ could have been in a very favorable situation in front of the target $105_A$ if he/she had already initiated a forward run, which could have resulted in a score.

Another Example of a Specific Embodiment

Figure 6:
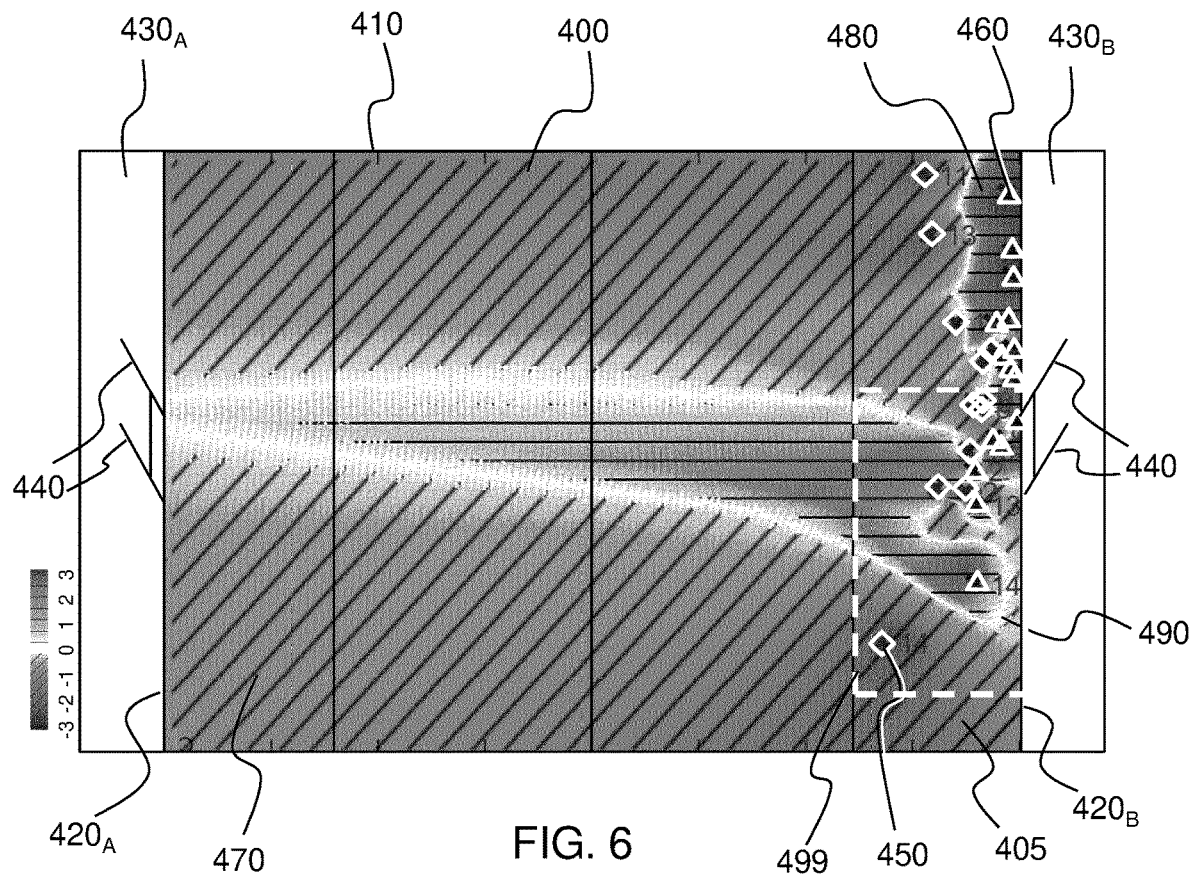
FIG. 6 is an example mapping obtained by another example of a method for analyzing dynamic occupancy according to the invention.

FIG. 6 is a mapping 400 obtained by a method for analyzing a dynamic occupancy of a sports field according to the invention. It should be emphasized that the analysis system implementing the analysis method is similar to that shown in FIG. 1.

In the present non-limiting example of the invention, the mapping 400 corresponds to an analysis of the dynamic occupancy of a rugby field 410 by two teams playing rugby union. The game accessory here is a rugby ball (not shown in FIG. 6), which has the particularity of being oval in shape.

The main object of the game for each team is to carry the rugby ball behind the touch line 420 defended by the opposing team, in order to touch the ground with the ball in a scoring area 430, commonly called the touch line, and thus score the points for a try. This action will later be referred to as "scoring a try".

Another object in the game is to kick the rugby ball between two posts 440 located symmetrically, on the opponent's touch line 420, in relation to the center of the touch line. This other object, corresponding to scoring a "drop", is generally secondary because it scores less points than a try.

In addition, it should be emphasized that a team scoring a try also has the option of getting extra points by "converting the try" with a set-piece attempt.

team A's players 450, defending the end area $430_A$ of the sports field 410 are shown in FIG. 6 as diamonds. team B's players 450, defending the end area $430_B$ of the sports field 410 are shown as triangles.

The mapping 400 is delimited in at least three areas:
an area 470 of dominance of team A, corresponding to the diagonally hatched areas on the mapping 400;
an area 480 of dominance of team B, corresponding to the horizontally hatched areas on the mapping 400; and
a neutral area 490, corresponding to the non-hatched areas on the mapping 400.

It should be emphasized that the area 470 is not continuous here.

The neutral area 490 corresponds to a buffer area between the two areas 470 and 480 of dominance of each team.

The occupancy of the area illustrated in FIG. 6 corresponds to a phase where the two teams A and B are in the area 405 of the sports field 410 known as the "22 meters" line of team B, near the touch line $420_B$. The occupancy of the sports field is favorable to team A, which forces team B to the touch line $420_B$.

Figure 7:
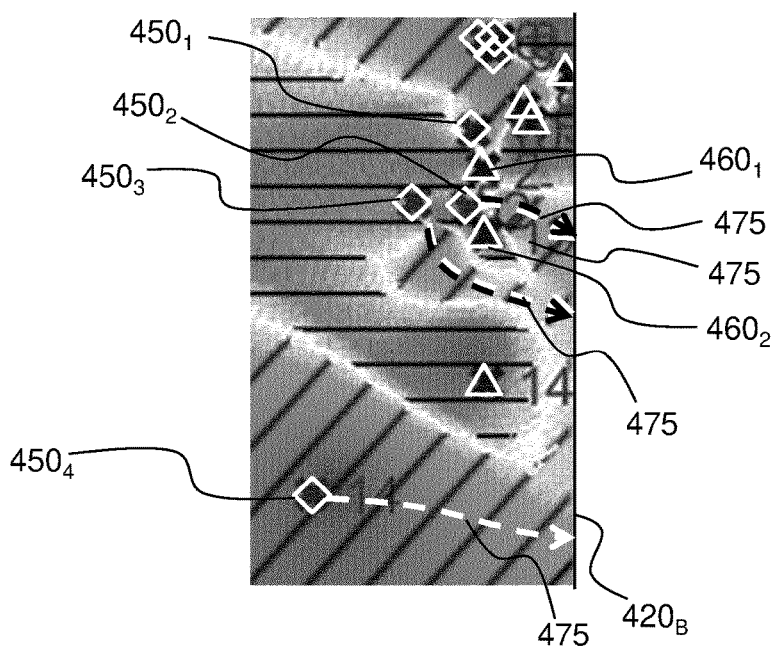
FIG. 7 is an enlargement of a part of the mapping of FIG. 6.

FIG. 7 is an enlargement of part 499 of the mapping 400.

Considering that the rugby ball is in the hands of player $450_1$, if player $450_1$ successfully passes to player $450_2$, player $450_2$ has the opportunity of scoring a try by sneaking between the opposing players $460_1$ and $460_2$, as shown in area 471 of the area of dominance 470.

However, if the ball is intercepted by the opposing player $460_1$, he/she has the option of running away to the scoring area $430_A$, to score a try for team B.

Player $450_1$ also has the opportunity of passing the ball to players $450_3$ and $450_4$ who are also in favorable positions to score a try.

In other words, the area of dominance 470 shows three paths 475 leading to team B's touch line $420_B$, these paths 475 corresponding to favorable actions for team A. If one of these paths 475 is followed by a player 450, team A will generally score a try.

It should be emphasized that if player $450_1$ passes the ball to his left, corresponding to the upper part of the area of dominance 470, team A would not be in a favorable position to score a try because team B players are well positioned defensively in that part of the sports field.

Figure 8:
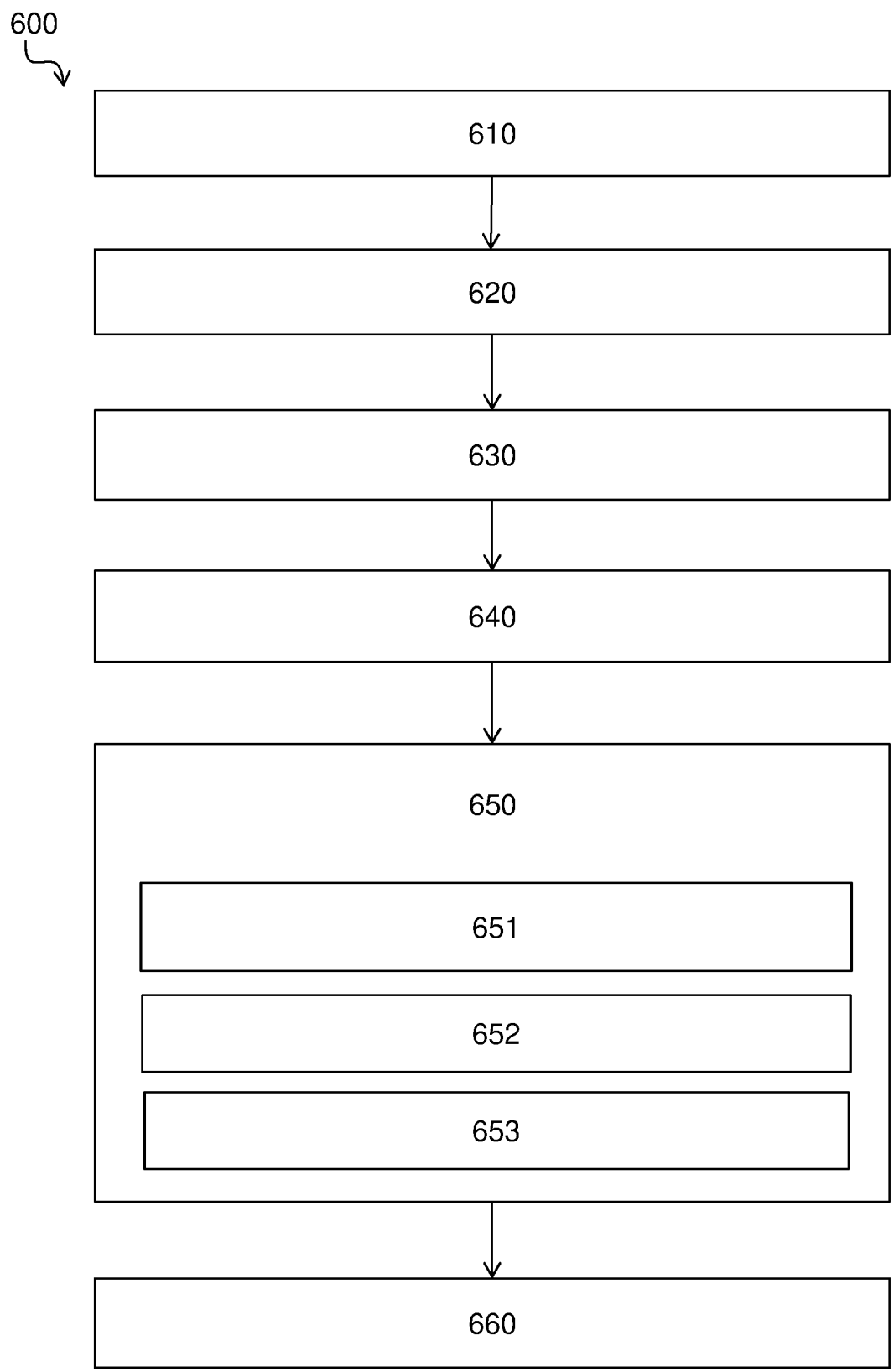
FIG. 8 is a synoptic diagram of the analysis method resulting in the mapping of FIG. 6.

The method 600 for analyzing the dynamic occupancy of the sports field, allowing the mapping 400 to be obtained, is illustrated in FIG. 8 in the form of a synoptic diagram.

The analysis method 600 comprises a first step 610 of acquiring a video stream by at least three cameras, advantageously fixed and each acquiring a part of the rugby field 410. It should be emphasized that the images obtained by each camera overlap in part in order to obtain a full image of the sports field 410.

From an analysis of the integral images of the sports field 410, the instantaneous position of each player 450 and 460 is obtained during a second step 620, similar to step 240 of the previous embodiment of the invention.

An instantaneous speed vector associated with each player present in the sports field 410 is also computed during a third step 630 from two successive positions of said player previously established during the second step 620.

The time of movement between the instantaneous position of each player in the sports field 410 and at least one point in the sports field 410 is determined during a fourth step 640 depending on the instantaneous speed vector and physical parameters associated with said player. These physical parameters include an acceleration characteristic of said player and a speed characteristic of said player.

It should be emphasized that the calculation of the time of movement can be performed only on part of the sports field, depending on the position of the players, in order to optimize the calculation time.

The method 600 then comprises a fifth step 650, generating the mapping 400 representing the dynamic occupancy of the sports field 410 by the two teams.

During this step 650, the sports field 410 is delimited into three areas: an area of dominance for each team and a neutral area. It should be emphasized that each area may be discontinuous or disjointed.

The area of dominance for each team, namely area 470 for team A and area 480 for team B, is computed in a sub step 651 of step 650.

The area of dominance of each team corresponds to the set of points in the sports field 410 for which a player of said team has a time ahead of the players of the opposing team greater than a predetermined threshold, the time ahead being equal to the difference between the time of movement of two players to the same point.

The neutral area is determined in a sub step 652 of step 650 and corresponds to the set of points in the sports field for which the difference between the minimum time of movement of each team is less in absolute value than the predetermined threshold (e.g., 0.1 s), the minimum time of movement of each team to a point in the sports field corresponding to the minimum value of the times of movement of the players of said team to that point.

In other words, the value of the predetermined threshold is used to delimit the limits of the three sports fields.

Generally, each area is associated with a distinct color, such as blue for area 470, red for area 480 and white for neutral area 490.

In this non-limiting example of the invention, step 650 also comprises a sub step 653 of determining a color intensity for different areas, the intensity depending on the maximum time ahead of the players of a team relative to the players of the opposing team. The greater the time ahead, the higher the intensity.

It should be emphasized that the color intensity values of the mapping form a continuous surface, whose color gradients are also continuous.

The resulting mapping 400, along with performance indicators, are then displayed in real time in a sixth step 660 of the method 600, on a display screen.

Another Example of a Specific Embodiment

Figure 9:
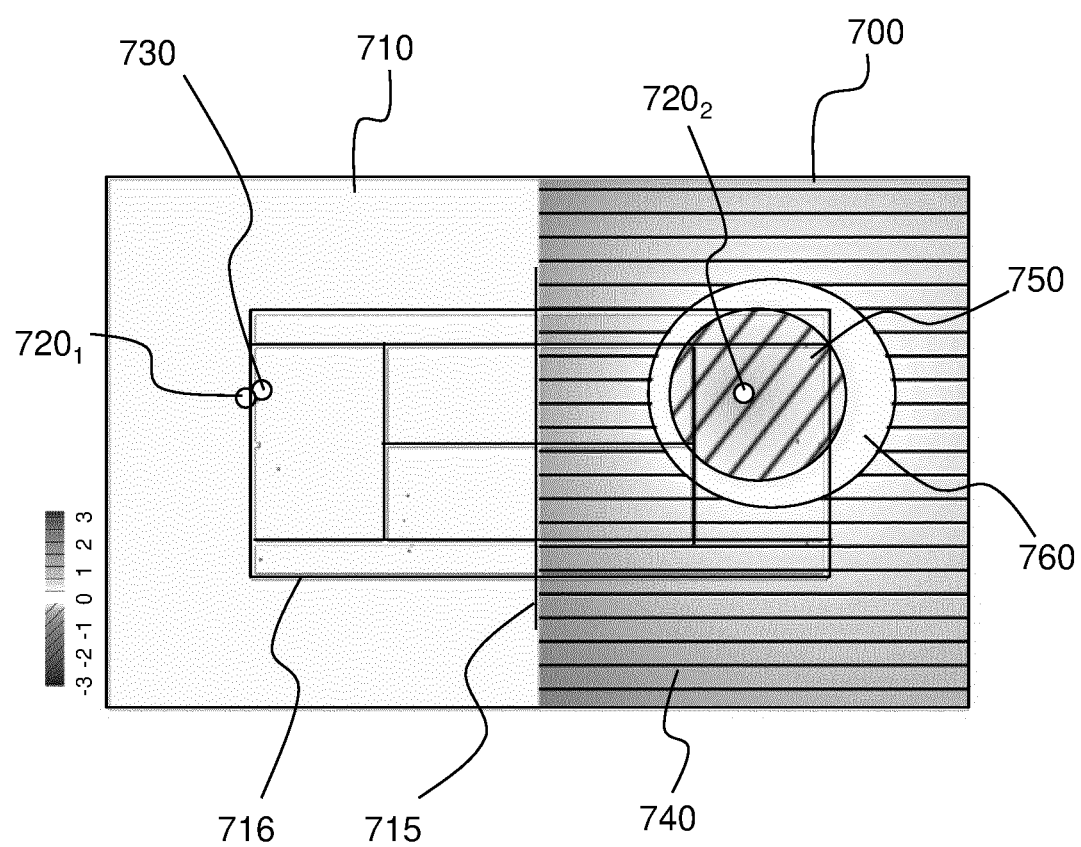
FIG. 9 is another example of a mapping obtained by a dynamic occupancy analysis method according to the invention.

FIG. 9 shows a mapping 700 of a dynamic occupancy of a tennis court 710, obtained by a method similar to that illustrated in FIG. 2 or FIG. 8. The analysis system implementing the analysis method is similar to that illustrated in FIG. 1.

In this non-limiting example of the invention, the mapping 700 is computed on half of the sports field 710, delimited by a net 715. The half of the sports field 710 considered corresponds to the half to the right of the net 715 in FIG. 9.

It should be emphasized that the calculation is not restricted to the interior marking 716 of the tennis court 710, but is also performed within a strip around the marking 716.

Two players 720 compete in a so-called "singles" match and exchange a ball 730, which is a moving game accessory. During a game, the point is generally scored by one player when the opposing player commits a foul with the ball. For example, a foul is committed when the first bounce of the ball after crossing the net is outside the markings of the singles court, or when the player returns the ball after two bounces in his/her half of the court.

In the phase of play illustrated in FIG. 9, the ball 730 is detected, or considered, for the player $720_1$ located to the left of the net 715 on the mapping 700, who will seek to return the ball into the opposing half of the court occupied by the player $720_2$.

In this non-limiting example of the invention, it should be emphasized that the two players 720 each form a separate team. In other words, each team comprises a single player.

Determination of the dynamic occupancy of the sports field is performed here on player $720_2$'s half of the sports field.

The mapping 700 is thus delimited into three areas:

- an area 740 of dominance of player $720_1$, shown in FIG. 9 by diagonal hatching;
- an area 750 of dominance of player $720_2$, shown in FIG. 9 by diagonal hatching;
- a neutral area 760 where no player is considered as dominant.

It should be emphasized that the three areas are computed according to a possible trajectory of the ball 730 and represent the possibility of player $720_2$ returning the ball.

For example, if the ball 730 is returned to the area 750, the player $720_2$ will have no trouble returning the ball and putting player $720_1$ in trouble. The player $720_2$ will therefore have a higher probability of scoring, by making a winning shot.

On the contrary, if the ball 730 is sent back to the area 740, the player $720_2$ will be in difficulty returning the ball 730, or will not be able to return it, which increases the probability of player $720_1$ scoring. The player $720_1$ thus makes a winning shot.

If the ball arrives in area 760, with neither player dominating, the exchange should a priori continue.

It is thus possible to identify where to send the ball 730 to make a winning shot when a favorable situation arises for one of the players 720.

Performance indicators may also be determined concomitantly with the mapping 700. Such indicators include, for example:

- the quality of court coverage prior to the opponent's move;
- the number of direct fouls, estimated by the actions in which the ball is incorrectly returned although it was received by a player in his/her area of dominance;
- the quality of each return of the ball;
- the return opportunities available at any time or over all or part of the game.

Other Advantages and Optional Characteristics

In variations of the foregoing embodiments, the mapping is delimited into at least four areas, including an area of dominance for each, a neutral area and a quasi-neutral area, in order to highlight sports fields weakly dominated by one of the two teams.

It should be emphasized that the subdivision is generally based on a comparison of the time of movement of at least one player on each team, or even the time of movement of the game accessory.

In variations of the foregoing embodiments, the analysis system includes a means of interaction for an individual to change some or all of the data associated with a movable element, such as the instantaneous position of the movable element or the instantaneous speed of the movable element to see the impact on the game phase being analyzed. Furthermore, the analysis system can be used on data of instantaneous positions and speeds, of all or part of the movable elements defined according to a scenario pre-set by a coach, in order to test different tactics in relation to at least one phase of play.

The invention claimed is:

1. A method for analyzing a dynamic occupancy of a sports field by a plurality of movable elements, a movable element being a player of one of two opposing teams of a game or a game accessory, such as a ball, a puck or a shuttlecock, each team comprising at least one player, the method comprising:
   - acquiring an instantaneous position for all or some of the movable elements in the sports field at at least two distinct points in time;
   - for each movable element, determining an instantaneous speed vector;
   - for each localized movable element, determining a time of movement between the instantaneous position of the movable element and all or part of the points on the sports field, depending on the instantaneous speed vector, and of a movement model associated with the movable element;
   - for each movable element located and for all or part of the points of the sports field, determining a time ahead of the movable element in the sports field at the point, comprising comparing the duration of movement of the movable element towards the point of the sports field with the duration of movement of another movable element towards the same point; and
   - for all or some of the located players, delimiting an area of dominance of the player in the sports field, the area of dominance comprising points in the sports field for which the time ahead of the player is greater than a predetermined threshold.

2. The method according to claim 1, further comprising delimiting the sports field into three areas: an area of dominance for each team and a neutral area, the area of dominance of a team comprising all areas of dominance of the players of the team, and the neutral area comprising points of all or part of the sports field not covered by an area of dominance of a team.

3. The method according to claim 1 wherein the area of dominance of a player of a team corresponds to the set of points on the sports field for which the player has a time ahead between the players of the opposing team greater than a predetermined threshold, the time ahead between two players being equal to the difference between the duration of movement of two players towards the same point.

4. The method according to claim 2 wherein the neutral area comprises points in all or part of the sports field where the time of movement of the game accessory is greater than the time of movement of at least one player of each team.

5. The method according to claim 1 wherein an area of dominance of a player of a team comprises a set of points of the sports field for which both:
   - the time of movement of the player to a point of the area of dominance is equal to the smallest of all times of movement of all players to that point, and
   - the time of movement of the game accessory to the same point of the area of dominance is less than the smallest of the times of movement of the players of the other team.

6. The method according to claim 1 wherein the movable elements whose instantaneous positions are acquired are only players, the method further comprising determining the instantaneous position of the game accessory as equal to the position of a player.

7. The method according to claim 1 wherein the sports field comprises two portions, the movements of each team being constrained within a separate portion of the sports field, and wherein the time ahead of a player is computed in relation to the players of his/her team and the game accessory, the time ahead being equal to the difference between the time of movement of the game accessory to the point and the time of movement of the player to that point.

8. The method according to claim 7, wherein the time ahead of a team at a point of the portion of the sports field occupied by the team corresponds to the maximum time ahead of the players of the team.

9. The method according to claim 7 wherein the area of dominance of a team in a part of the sports field occupied by the opposing team comprises a set of points of the part of the sports field for which a time ahead of the game accessory to the point is greater than a predetermined threshold, wherein the time ahead of the game accessory is the difference between the smallest of the times of movement of the players of the opposing team and the time of movement of the game accessory.

10. The method according to claim 1 further comprising a step of generating a mapping representing the occupancy of the area by each team.

11. The method according to claim 10, wherein said generating a mapping comprises a sub step determining a color intensity depending on player dominance, with each team represented by a distinct color.

12. The method according to claim 10 wherein the generation of the mapping is performed in real time.

13. The method according to claim 1 further comprising acquiring a video stream by at least one camera covering all or part of the sports field, and wherein said acquiring the instantaneous position of the game accessory comprises analyzing the video stream to determine the instantaneous position.

14. The method according to claim 13, wherein said acquiring the instantaneous position of each player comprises analyzing the video stream to determine the instantaneous position.

15. The method according to claim 13 wherein the mapping is synchronized and overlaid on the video stream.

16. The method according to claim 13 further comprising tracking all or part of the players and/or game accessory in the video stream.

17. The method according to claim 13 further comprising:
displaying the video stream in real time, on which at least one player tracking indicator is superimposed; and
repositioning the at least one tracking indicator by an operator.

18. The method according to claim 1 wherein said acquiring the instantaneous position of each player and/or game accessory in the sports field comprises analyzing a signal emitted by a tracker attached to the player and/or game accessory and received by at least one terminal located in the vicinity of the sports field.

19. The method according to claim 1 further comprising determining at least one quantitative indicator of a qualitative characteristic of a player selected from:
a value representing the player's dominance in at least one part of the sports field, computed from the characteristics of the areas of dominance recorded during a match;
a passing quality of the game accessory;
a value representing the pressure experienced by the player;
a quality of hitting the playing accessory; and
a direct foul rate.

20. A system for analyzing a dynamic occupancy of a sports field by two opposing teams of a game that implements the method according to claim 1, comprising:
means for processing data by a computer comprising a processor and a computer memory;
means for acquiring the instantaneous position of a movable element in the sports field, the movable element being a player or the game accessory;
means for determining a value representing a time ahead of a movable element at a point in the sports field in relation to another movable element; and
means for delimiting an area of dominance of a player in the sports field, the area of dominance comprising a set of points for which the player has a time ahead greater than a predetermined threshold.

21. The system according to claim 20, wherein the means for acquiring the instantaneous position of each movable element comprises at least one camera acquiring a video stream covering all or part of the sports field, and/or at least one tracker attached to the movable element and at least one terminal for receiving a signal emitted by the tracker.

22. The system according to claim 20 further comprising means for generating and displaying a mapping representing the dynamic occupancy of the sports field.

23. The system according to claim 20 further comprising means for recording the acquired data and for modifying by a user of all or part of the recorded data of instantaneous positions and/or speeds of the movable elements.

* * * * *